United States Patent [19]

Stroh et al.

[11] Patent Number: 5,714,168
[45] Date of Patent: Feb. 3, 1998

[54] METHOD FOR INCREASING FLOWABILITY OF SPRAY DRIED VITAMIN POWDERS HAVING LOW VITAMIN CONCENTRATIONS

[75] Inventors: Friedemann H. Stroh, Southgate; Rudolph E. Lisa, Gross Ile, both of Mich.

[73] Assignee: BASF Corporation, Mount Olive, N.J.

[21] Appl. No.: 733,231

[22] Filed: Dec. 11, 1996

[51] Int. Cl.$^6$ ............................................. A61K 9/16
[52] U.S. Cl. ...................... 424/490; 424/479; 424/458; 424/461; 424/493
[58] Field of Search ............................ 424/490, 458, 424/252, 479, 493, 461

[56] References Cited

U.S. PATENT DOCUMENTS 4,486,435  12/1984  Schmidt et al. ............... 424/252
5,000,888   3/1991  Kilbride et al. ................ 264/7

Primary Examiner—Thurman K. Page
Assistant Examiner—William E. Benston, Jr.
Attorney, Agent, or Firm—Joanne P. Will

[57] ABSTRACT

The present invention relates to a method for increasing the flowability of spray dried vitamin powders having low vitamin concentrations and high concentrations of a maltodextrin carrier by coating said low concentration vitamin powders with hydrophobic silica.

6 Claims, No Drawings

METHOD FOR INCREASING FLOWABILITY OF SPRAY DRIED VITAMIN POWDERS HAVING LOW VITAMIN CONCENTRATIONS

FIELD OF THE INVENTION

The present invention relates to a method for increasing the flowability of spray dried vitamin powders having low vitamin concentrations and a high concentration of maltodextrin or maltodextrin and sugar as a carrier.

BACKGROUND OF THE INVENTION

An important property of any vitamin powder is its flowability. Poor flowability causes the powder to stick to surfaces, making it difficult to handle. Further, poor flowability will lead to an undesired inhomogeneous distribution of the vitamin powder in the final vitamin powder blend. This is particularly true of microingredients—those that are present at very low levels. Flowable vitamin powders can be prepared by spray drying according to methods known to those skilled in the art. When spray drying vitamin active ingredients with carrier materials, normally the goal is to have as much active ingredient in the vitamin product as possible.

In vitamin powders containing high concentrations of active ingredients (greater than 40%), a typical carrier is maltodextrin. A coating agent such as silica is used to enhance the flowability of the high concentration product. See, U.S. Pat. No. 4,486,435 which specifically discloses free flowing vitamin powders for tabletting comprising a high concentration vitamin active ingredient, i.e. 45–60% vitamin active ingredient, 10–60% maltodextrin as an encapsulating agent and 0.2–2% hydrophobic silica.

However, there are special cases where it is desirable to have a low concentration of vitamin active ingredient, i.e. less than 10% by weight. For example, biotin is an active ingredient which is useful in small amounts. However, special problems arise when blending spray dried vitamin compositions. To insure homogeneity in the final vitamin powder blend, spray dried vitamin powders should be highly flowable. This is particularly important for low concentration vitamin powders.

Thus, there is a need in the art for vitamin powders having low vitamin concentrations and the desirable free flowing properties. Applicants have succeeded in producing maltodextrin based vitamin powders having low vitamin concentrations and free flowing properties better than the current art.

DEFINITIONS AND USAGES OF TERMS

The term "flowability", as used herein, refers to how free flowing a powder is. Specifically, free flowing powders have a FLODEX flowability of 50 or more. The FLODEX flowability test is described in detail in U.S. Pat. No. 5,000,888, column 7, lines 55–70, column 8, lines 1–45, incorporated by reference herein

SUMMARY

The present invention relates to a process for improving the flowability of spray dried vitamin powders wherein said vitamin powders are comprised of maltodextrin or maltodextrin and sugar carriers and low concentrations of vitamins, comprising coating said vitamin powders with hydrophobic silica.

DETAILED DESCRIPTION

The present invention relates to a process for improving the flowability of spray dried vitamin powders wherein said vitamin powders are comprised of maltodextrin or maltodextrin and sugar carriers and low concentrations of vitamins, comprising coating said vitamin powders with hydrophobic silica.

The Process of the Present Invention

Low levels of vitamins, the carriers, i.e., maltodextrin or a maltodextrin and sugar blend, and hydrophobic silica are blended with water, and spray dried according to methods known to those skilled in the art. Spray Drying Methods useful in the practice of the present invention are described in Masters, K., *Spray Driers Handbook*, 5th edition, Wiley, N.Y., 1991.

Vitamins

Vitamins useful at low levels include, but are not limited to, Vitamin C, all the B vitamins, A, D, E, and K, biotin, and folic acid. More preferably, biotin, folic acid, and vitamin K; and most preferably biotin. Preferably, the vitamin concentration is from about 0.1–10%, more preferably from about 0.1–5%, most preferably from about 0.1–2%.

Maltodextrin

Maltodextrin is the carrier useful in the practice of the present invention. It can be obtained from GPC under the Trade name of MALTRIN M180, M150, M100, M50 or M40. It is preferably used at a level of about 60–99.9%, more preferably about 90–99.9%, most preferably about 96–99.9%. Further, sugars can be blended with the maltodextrin to produce a maltodextrin and sugar blend. Sugars useful for blending with maltodextrin include, but are not limited to, glucose, sucrose, fructose, lactose and dextrose.

Hydrophobic Silica

Hydrophobic silica can be obtained from Degussa under the Tradename of SIPERNAT D17. It is preferably used at a level of 0.1–5%, more preferably 0.2–2%, most preferably 0.5–1%.

Optional Ingredients

The present invention may optionally contain densifiers such as, but not limited to, calcium silicate, calcium phosphate, calcium sulfate, or barium sulfate and preservatives such as, but not limited to, sodium benzoate or potassium sorbate at levels of about 0–18%.

Thickeners

The present invention may optionally contain thickeners such as, but not limited to, pectin, gum arabic, celluloses, plant gums, gelatin, polyvinylpyrrolidone (pvp) at levels of about 0–5%.

All percentages are weight percent on a dry basis unless otherwise indicated.

The Utility of the Present Invention

The utility of the present invention is determined by measuring the flowability of the low concentration vitamin containing powders produced as described hereinabove. Flowability can be measured with the FLODEX method (Dow-Lepetit). A sample is placed in a smooth cylinder with a circular hole in the bottom. The whole is closed during filling. Once the complete amount of powder is filled in, the bottom hole is opened. A powder with a good flowability will flow through a small hole, whereas a powder with a poor flowability requires a large hole to leave the cylinder. The FLODEX value is the reciprocal of the diameter in millimeters times 1000 of the smallest hole through which the sample will pass. The maximum flowability is obtained in this test utilizing a flow disc having a four millimeter diameter orifice. In this case, the flow obtained is reported as equal to a value of 250. One skilled in the art understands that the value of 250 could imply a higher flowability because the standard flow disc orifices will only measure up to 250. A preferred flowability range is 100 to 250, more preferred 167 to 250, most preferred 200 to 250.

EXAMPLE 1

(Hydrophobic Silica)

Biotin 2% SD with SIPERNAT D17 (hydrophobic silica)

In a five gallon tank heated utilizing a hot plate, 41% by weight of maltodextrin (MALTRIN M180) and 1% by weight pectin are added to 57.1% by weight of water and stirred at 60° C. After the maltodextrin is dissolved, 0.9% by weight of Biotin is added and dispersed in the mixture. Utilizing a pilot sized spray drying apparatus, e.g a Niro utility unit, the previously prepared suspension is metered to the 5 inch diameter atomizer wheel at a wheel speed of 19,000 RPM. A silica cloud is maintained in the spraying chamber by screw feeding SIPERNAT D17, a hydrophobic silica from Degussa, to provide a coating. The silica coating constitutes about 1% of the total weight of the particles. The FLODEX of the resulting off-white free flowing powder is 200.

EXAMPLE 2

(Hydrophilic Silica)

Following the procedure of Example 1, a spray dried biotin 2% powder was prepared. As a substitute for hydrophobic silica utilized in Example 1, AEROSIL 200, a hydrophilic silica from Degussa was utilized. The FLODEX flowability value is 42.

EXAMPLE 3

(Plant Scale Run with Hydrophobic Silica)

A vessel was charged with 1965 lbs. water and heated via hot jacket to 135° F. 2308 lbs of MALTRIN M180 were charged to the vessel and dissolved using a homogenizer. To this was added 45 lbs pectin and 55 lbs biotin. The batch was mixed for another 45 minutes at 135° F. This liquid feed was pumped at a pressure of about 1500 psig to maintain a flow rate of about 12 lbs/hr through a SB-58 Delavan atomizing nozzle (0.058 inch orifice) into a 12 foot diameter commercial spray drying tower. The air inlet temperature was maintained at about 360° F. and air outlet temperature was about 200° F. SIPERNAT D17 hydrophobic silica was added to the drying chamber via a screw feeder at a rate of about 6 lbs/hr. The batches with the lot numbers 6213433, 6213434, and 6214435, in the TABLE below, were produced according to the spray processes described hereinbelow.

TABLE

| Biotin 2% Lot # | HLR 501002 | HLR 502003 | HLR 501014 | BASF 6213433 | BASF 6213434 | BASF 6214435 |
|---|---|---|---|---|---|---|
| FLO-DEX | 45 | 63 | 63 | 250 | 250 | 250 |

*HLR = Hoffman La Roche

Clearly, the Applicants invention improves flowability of the low concentration vitamin powders.

We claim:

1. A process for improving the flowability of spray dried vitamin powders wherein said vitamin powders are comprised of maltodextrin or maltodextrin and sugar carriers, optionally thickeners and densifiers, and low concentrations of vitamins, comprising the steps of:

(a) dissolving said maltodextrin or maltodextrin and sugar carriers and other optional ingredients in an aqueous environment to form a suspension;

(b) adding said low concentrations of vitamins to the suspension formed in step (a);

(c) spray drying said suspension formed in step (b)

(d) coating said spray dried suspension formed in step (c) with hydrophobic silica.

2. A process according to claim 1, wherein said flowability is in the range of 100 to 250.

3. A process according to claim 2, wherein said vitamin is biotin.

4. A process according to claim 3, wherein said low vitamin concentration is 0.1–2%.

5. A process according to claim 4, wherein said maltodextrin is at a level of 96–99.9%.

6. A process according to claim 5, wherein said hydrophobic silica is at a level of 0.5–1%.

* * * * *